United States Patent
Jacobs et al.

(10) Patent No.: US 8,187,558 B2
(45) Date of Patent: May 29, 2012

(54) CONTAINERS FOR REDUCING OR ELIMINATING FOAMING

(75) Inventors: Merrit N. Jacobs, Fairport, NY (US); Nicholas Van Brunt, Rochester, NY (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 0 days.

(21) Appl. No.: 12/834,088

(22) Filed: Jul. 12, 2010

(65) Prior Publication Data

US 2010/0276445 A1 Nov. 4, 2010

Related U.S. Application Data (62) Division of application No. 11/153,098, filed on Jun. 15, 2005, now abandoned.

(51) Int. Cl.
*B01L 3/02* (2006.01)
(52) U.S. Cl. .......................................... 422/512
(58) Field of Classification Search .................... 422/102
See application file for complete search history.

(56) References Cited

U.S. PATENT DOCUMENTS

| | | | | |
|---|---|---|---|---|
| 3,564,256 A | * | 2/1971 | Arlman et al. | 250/432 R |
| 5,122,272 A | * | 6/1992 | Iana et al. | 210/473 |
| 5,431,813 A | * | 7/1995 | Daniels | 210/282 |
| 5,646,049 A | | 7/1997 | Tayi | |
| 6,684,680 B2 | * | 2/2004 | Pierskalla et al. | 73/1.03 |
| 7,378,057 B2 | | 5/2008 | Arter et al. | |
| 7,569,189 B2 | | 8/2009 | Jacobs et al. | |
| 7,846,395 B2 | | 12/2010 | Shaw | |
| 8,026,101 B2 | | 9/2011 | Bower et al. | |

FOREIGN PATENT DOCUMENTS

| | | |
|---|---|---|
| JP | 63-172955 A | 7/1988 |
| JP | 63-27865 A | 11/1994 |
| JP | 2003-329688 A | 11/2003 |
| WO | 03/084664 A1 | 10/2003 |
| WO | WO 2004/073468 | 9/2004 |

OTHER PUBLICATIONS

European Search Report, Dated Nov. 7, 2006 for European Appln. No. EP06253072.

* cited by examiner

*Primary Examiner* — Bobby Ramdhanie
(74) *Attorney, Agent, or Firm* — Todd J. Burns (57) ABSTRACT

A method for reducing or eliminating the aspiration of foam into a metering probe includes the steps of providing a reagent supply container having a baffle having sealed ends and having a liquid reagent in it. A metering probe movable in a direction toward and away from the reagent supply container is provided. A closure is moved away from the opening of the container and both seals covering the first and second openings of the baffle are pierced allowing liquid to enter the baffle from the end of the baffle submerged in the liquid thereby providing a foam reduced or foam free zone. The metering probe is moved into the first opening of the baffle and into contact with the liquid in the baffle. A selected amount of liquid in the baffle is aspirated and the metering probe is moved out of the baffle.

16 Claims, 5 Drawing Sheets

CONTAINERS FOR REDUCING OR ELIMINATING FOAMING

CROSS REFERENCE TO RELATED APPLICATIONS

This patent application is a divisional of U.S. Non-Provisional application Ser. No. 11/153,098 filed Jun. 15, 2005, now Abandoned, the disclosure of which is incorporated by reference in its entirety.

BACKGROUND OF THE INVENTION

The present invention relates to reducing or eliminating foaming in a liquid containing container, particularly where the liquid is removed from the container. In particular, the present invention relates to a reagent supply or pack for use on an automated analyzer, which reduces or eliminates foaming.

Figure 1:
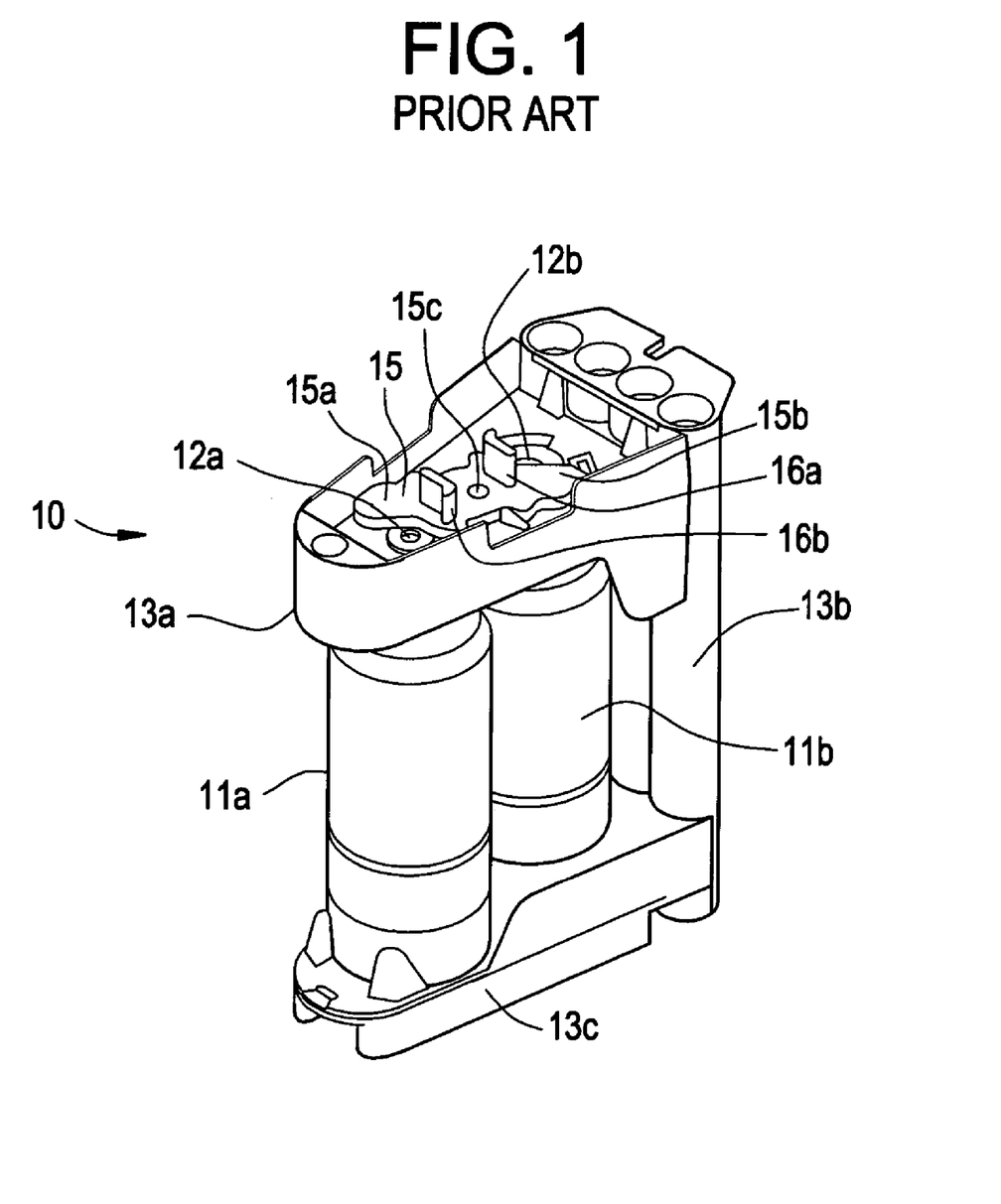
FIG. 1 is a perspective view of a reagent pack or supply container known in the art.

Known diagnostic analyzers include immunodiagnostic and clinical chemistry analyzers such as the Vitros® ECi immunodiagnostic analyzer, sold by Ortho-Clinical Diagnostics, Inc. These types of analyzers include a source of reagents for carrying out various tests. Most often, the reagents are stored in containers having removable closures in which a metering probe can be inserted to aspirate a reagent in the container. For example, a reagent pack container as shown in FIG. 1 is used on the Vitros® ECi immunodiagnostic analyzer, sold by Ortho-Clinical Diagnostics, Inc. In the containers, such as those shown in FIG. 1, a Surlyn® seal is at the top of the container to prevent leakage of the reagents. The seal is generally broken before first use.

In the known containers, foam occurs in reagents during shipment and handling. In many known metering systems, foaming is mitigated by aspirating from the bottom of the liquid using a non-disposable washed reagent metering probe. However, aspirating from the bottom of the container can cause increased metering imprecision. In addition, while the small diameter and geometry of the non-disposable reagent metering probe (also known as a proboscis) enables aspiration from the bottom of the reagent pack, the trend in modern analyzers is to use a disposable tip which makes it much more difficult to aspirate from the bottom of the reagent container because of the size of the tip and the need to minimize the wetted depth of the tip. Since the tip cannot be inserted very far into the liquid, there is the significant possibility that the metering probe will aspirate foam instead of pure reagent liquid.

Known containers for controlling evaporation include those described in U.S. Patent Application Publication No. 2003/0223914 A1.

None of the known art described above, adequately addresses resolving the problems described above, in particular, preventing or reducing the aspiration of foam into a metering probe. For the foregoing reasons, there is a need for a container that can reduce or eliminate the formation of foam, at least in the area where liquid is aspirated by a metering probe.

SUMMARY OF THE INVENTION

The present invention is directed to a method that solves the foregoing problems of reducing or eliminating the aspiration of foam or the presence of foam in a container.

One aspect of the invention is directed to a foam reducing or eliminating container for containing a liquid. The container includes: a container body having a top portion, a bottom portion and an opening for adding a liquid to or removing a liquid from the container body; and a hollow baffle located within the container with first and second openings therein, the first and second openings being covered with a pierceable seal, wherein the first opening of the baffle is at least partially aligned with the opening of the container.

According to another aspect of the invention, there has been provided a reagent supply container for an automated analyzer. The reagent supply container includes: a container as described above; and a closure which is movable away from the opening of the container to be in an open position and movable into contact with the opening to be in a closed position.

According to another aspect of the invention, there has been provided a reagent supply for an automated analyzer. The reagent supply includes: the reagent supply container as described above; and a liquid reagent therein, wherein the second opening of the baffle is submerged in liquid.

According to yet another aspect of the invention, there has been provided a reagent supply for an automated analyzer. The reagent supply includes: a reagent supply container which includes a container body having side walls, a bottom, and a top, the top having an opening for adding a liquid reagent to or removing the liquid reagent from the container body, and a tubular baffle located within the container, the baffle having sidewalls and a first and second openings at opposite ends thereof, both first and second openings of the baffle having a pierceable seal, wherein the exterior surface of the baffle sidewalls contacts the opening of the container with the opening of the container body; a closure which is movable away from the opening of the container to be in an open position and movable into contact with the opening to be in a closed position; and a liquid reagent within the reagent supply container.

According to still another aspect of the invention, there has been provided an automated analyzer. The analyzer includes: a sample supply source; a sample metering station; a reaction vessel; a reagent supply as described above; and a measuring instrument for measuring a property of the sample.

According to yet another aspect of the invention, there has been provided a method for reducing or eliminating the aspiration of foam into a metering probe. The method includes: providing a reagent supply as described above; providing a metering probe movable in a direction toward and away from the reagent supply; moving the closure away from the opening of the container; piercing both seals covering the first and second openings of the baffle allowing liquid to enter the baffle from the end of the baffle submerged in the liquid, wherein the seals may or may not be pierced with the metering probe; moving the metering probe into the first opening of the baffle and into contact with the liquid in the baffle; aspirating a selected amount of liquid in the baffle; moving the metering probe out of the baffle.

According to still another aspect of the invention, there has been provided a method for manufacturing a reagent supply. The method includes: adding a liquid reagent to a container having an opening; providing a hollow baffle having side walls, a second opening sealed with a pierceable seal in the vicinity of a second end of the baffle, and a first opening optionally sealed with a pierceable seal in the vicinity of a first end of the baffle; inserting the sealed second opening of the baffle into the opening of the container to a point below the surface of the liquid; securing the side walls of the baffle to the container; and sealing the first opening of the baffle with a pierceable seal if it is not already sealed.

Further objects, features and advantages of the present invention will be apparent to those skilled in the art from detailed consideration of the preferred embodiments that follow.

BRIEF DESCRIPTION OF THE DRAWINGS

FIGS. 3 A and B are side cutaway schematic views of a baffle tube according to preferred embodiments of the present invention.

DETAILED DESCRIPTION OF PREFERRED EMBODIMENTS

The present invention includes a container body that has an opening, preferably at the top, to allow for the addition and withdrawal of liquid. A hollow baffle is also provided that includes first and second openings. The baffle helps to reduce or eliminate the buildup of foam in the container as explained more fully below. The hollow baffle is located in the container such that the first opening of the baffle is at least partially aligned with the opening of the container body. In operation, the second opening of the baffle will be under the surface of the liquid allowing the liquid, when the container contains liquid, to enter the baffle. The alignment of the container opening and the first opening allows a device, such as a metering probe, to be inserted into the interior of the baffle to withdraw liquid.

In a preferred embodiment, the baffle has sidewalls and a first and second end region, containing the first and second openings, respectively. The second end region of the baffle is inserted into the opening of the container, such that the second opening is below the surface of the liquid in the container. The liquid can enter the baffle through the second opening. The first opening of the baffle is located at a first end region of the baffle.

In a preferred embodiment the baffle is a tube. The first and second openings of the baffle are covered with a liquid impermeable pierceable sealing material such as Surlyn® an ethylene methacrylic acid co-polymer, available from DuPont, Inc. The seals are pierced before use as described below. As used herein, "pierce" is defined as creating an opening in the seal, such as by puncturing, cutting, scrapping, removing, etc. In one embodiment the baffle may be configured so that the first end region is raised slightly above the top portion of the container. In such an embodiment, the pierceable seal may optionally not be sealed to the baffle. Instead, the seal material is only sealed to the top portion of the container. The result is the film will be simply stretched over the first opening of the baffle. Having the first end region raised slightly above the top portion of the container will assist in assuring there is a tight seal.

As explained above, when the baffle is inserted into the container the second opening should be under the surface of the liquid to allow the liquid to enter the baffle. Since the pressure in the baffle and container should be equivalent, e.g., ambient pressure, as will be described below, the height of the liquid in the container and baffle will be equivalent. A suitable device, such as a metering probe can be inserted into the baffle to withdraw the liquid that is in the baffle.

As explained above, the second opening will be under the surface of the liquid. During transport and handling, foam may be generated in the liquid in the container. When the liquid is ready for use, the second seal will be pierced. Since the second opening is below the surface of the liquid, and hence, below the foam, only liquid will flow into the baffle, thus providing a foam reduced or foam free zone from which liquid can be withdrawn from the container. As used herein, the term to "reduce" or "eliminate" foam refers to the relative absence of foam in the baffle vis-à-vis the rest of the container as described above.

Thus, an important aspect of the invention is to have the second opening and pierceable seal of the baffle to be located below the surface of the liquid. The second opening should be below the surface of the liquid as far as possible to prevent the possible influx of foam into the baffle. However, the sealed tube cannot be of such a length that when it is inserted into the container during manufacture, the sealed tube displaces excessive amounts of liquid, possibly causing overflow of liquid out of the container. Also, if the second opening is on the bottom of the baffle, the baffle should not extend all the way to the bottom of the container in order to prevent a seal from being formed between the baffle and bottom of the container in a manner that would cause the container to form a seal with the baffle. Thus, in a preferred embodiment, the sealed tube should go as far below the surface as possible to prevent influx of foam but not overly displace the liquid in the container or contact the bottom of the container. Depending on the container, different length baffles can be used to achieve these objectives. In one preferred embodiment, the second opening is in the vicinity of the bottom of the container, more preferably two millimeters or less, most preferably around one millimeter from the bottom of the container.

In another preferred embodiment, the first opening of the baffle is in the vicinity of the container opening as described in connection with the figures below. In such an embodiment, the pierceable seal may cover both the first opening and container opening. The sidewalls of the baffle contact the container body in the vicinity of the container opening and more preferably at the container opening. The sidewalls may or may not form a seal with the container body. In a preferred embodiment, as described below, an air gap will be provided between the sidewalls of the baffle and container opening. Preferably, the container will include a lip at the opening and the baffle will also have a lip and the lips have mating surfaces. A protrusion or nib extending from the outer wall of the baffle may also be provided to provide for frictional engagement of the baffle with the container body.

One significant consideration is to allow air into the cavity or space above the liquid outside of the inserted baffle in order to equalize pressure from both inside the baffle, which will be at ambient pressure when the seal covering the first opening (i.e., first seal) is punctured, and the interior of the container outside the baffle. A first preferred embodiment for achieving equalization includes forming an air tight seal between the first opening of the baffle and opening of the container. This can be achieved by an air tight fit between the baffle sidewalls and the opening of the container. Alternatively, if an air tight fit in this manner is not desirable, the pierceable seal, which, as described above, extends over both the opening of the container and the first opening of the baffle is pierced only over the baffle first opening, leaving the seal intact over the area between the baffle sidewall and container opening.

These embodiments only allow ambient air above the liquid in the container when the liquid level in the baffle falls low enough to allow air to bubble up from the second opening of the baffle to the top of the liquid level. There is some risk that the air entering the liquid in this manner could create new bubbles, however, it is unlikely that they will create them inside the baffle interior itself. Tilting the container to the side (or angling the bottom of the tube as described in connection with FIG. 3B below) will for some fill levels result in a clear path for the air and the baffle will fill with liquid to a point above the second opening of the second baffle until the analyzer starts to use this liquid. At that point the liquid level will eventually drop again to the bottom of the tube and air will once again bubble from the second opening of the baffle into the interior of the container.

Another embodiment for achieving equalization includes providing a vent or opening near the first end region of the baffle for air to enter above the liquid level in the container after the first seal is broken. As noted above, there will be a vent or opening near the first end region to provide an air gap to allow the air pressure to equilibrate above the liquid in the bottle.

In one embodiment to achieve equalization, the first end region of the baffle, e.g., baffle sidewalls and the top portion of the container are in a sealing relationship. This can be achieved as described above, i.e., an air tight fit between the baffle sidewalls and the opening of the container, or the pierceable seal extending over both the opening of the container and the first opening of the baffle, with the seal being pierced only over the baffle opening, leaving the seal intact over the area between the baffle sidewall and container opening. In this embodiment, a vent or opening is provided in the baffle near the first end region. The vent can simply be a hole in the baffle sidewall. However, if the vent is not initially sealed, liquid from the interior of the container may enter into the sealed baffle during transport and storage. To prevent this from happening, it is preferred that the hole or vent be sealed during storage and opened before use.

In a particularly preferred embodiment, a gap or indentation, such as a crease or seam along the outer surface of the baffle sidewall will be provided between the baffle sidewall and the opening of the container to allow air into the space between the container and the surface of the liquid once the pierceable seal has been punctured over the gap. This is described in more detail in connection with FIGS. 3, 5 and 6.

In a preferred sequence, the initial process is to pierce the seals covering first and second openings in the baffle. After these seals have been removed or broken, the seal covering the hole or vent in the baffle sidewall can be removed or broken. This can be done in any suitable fashion. For example, a clean tip can be used (so as not to contaminate the top of the container with reagent). The clean tip is moved laterally relative to the baffle. The lateral movement opens the vent (i.e., the gap between the baffle sidewall and container) by piercing the seal in the region of the gap. The top portion of the container will need to be configured so that there is a region where the tip can be positioned to pierce the seal. Other suitable means for piercing the baffle vent seal can include separate slitter device or a protrusion that is part of the slidable shutter that covers the opening of the container as described below in connection with FIG. 1. In this embodiment, the seal is pierced as the shutter moves to an open position, the protrusion, which can have a sharp region that extends from the bottom of the shutter, will pass over the seal and open the seal.

The container and baffle of the present invention is preferably used in a reagent supply or pack for an automated analyzer. As used herein "reagent supply" and "reagent pack" are synonymous. In addition to the baffle and container described above, the container will also have an opening that is movable from a closed to an open position. Typically openings can include slidable shutter type openings, such as described in copending application Ser. No. 11/093,606 entitled "Opening and Closing a Container" by Merrit Jacobs et al. filed Mar. 30, 2005, incorporated herein by reference in its entirety or screw cap type openings such as shown in copending application U.S. Ser. No. 10/621,430 filed Jul. 16, 2003 also incorporated herein by reference in its entirety. As noted above, the second opening of the baffle is below the surface of the liquid reagent in the container. The first baffle opening and container opening is sized to allow the metering probe of the automated analyzer to be inserted into the container and interior of the baffle. The probe is lowered until the probe tip, which is preferably disposable, reaches the surface of the liquid reagent in the baffle. Thereafter, the reagent can be aspirated into the probe. The probe is then withdrawn and the reagent can be dispensed at another appropriate location, such as a reaction vessel, as described more fully below.

The automated analyzer usable with the present invention may include a sample supply source, a sample metering station, a reaction vessel, the reagent source described above, a reagent metering station and an instrument for measuring a property of the sample, such as a photometer or luminometer. In a preferred embodiment, the sample metering station and the reagent metering station are the same.

Another aspect of the invention provides a method for aspirating a liquid into a metering probe to reduce or eliminate the aspiration of foam into the metering probe. A metering probe as described in more detail below, preferably having a disposable tip, is moved toward the reagent source. The closure on the container body of the reagent source is moved away from the container, such as by sliding or unscrewing. Both of the seals are pierced (if they are not already pierced). The first and/or second seal may be pierced by the tip of the metering probe. The seal(s) may also be pierced by any other suitable device or method.

Upon contact with the surface of the liquid in the baffle, the pump of the probe will aspirate a selected amount of liquid into the probe, which, of course, depends on the liquid being aspirated. Upon aspiration of liquid into the probe, the probe is withdrawn from the container. The container closure is moved back to a position that covers the container opening. The metering probe is then moved relative to the analyzer and the aspirated liquid is dispensed into the desired location, such as a reaction cuvette, which may or may not already contain sample or reagent.

Now reference will be made to the non-limiting preferred embodiments shown in the figures. FIG. 1 is a known reagent pack container used on diagnostic analyzers such as the Vitros® ECi analyzer described above. As FIG. 1 shows, the container includes two reagent bottles or containers 11a and 11b having openings 12a and 12b, respectively. A frame 13a, 13b and 13c are used to contain the reagent bottles and to provide support for the slidable shutter closure. The vertical support 13b can be constructed in a tubular fashion in order to hold reaction wells. A sliding shutter closure 15 is mounted on the top of the reagent pack 10. In the embodiment according to FIG. 1, a single bifurcated slidable shutter having two sections 15a and 15b is used for each opening 12a and 12b, respectively. The shutter is rotatably anchored to the reagent pack by pin 15c. The shutter is moved by an opener that engages tabs 16a and 16b.

Figure 2A:
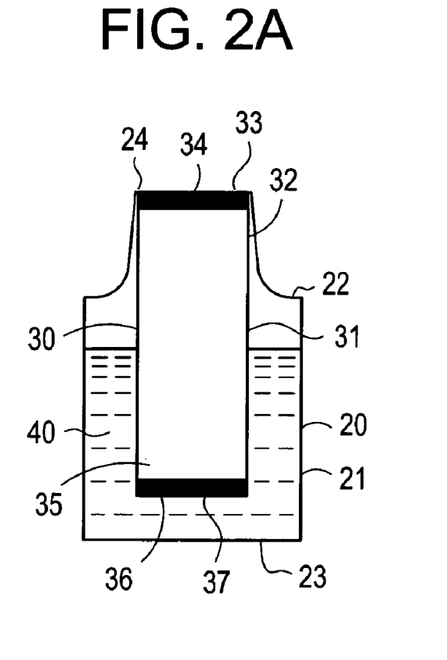
FIG. 2A is a side cutaway schematic view of a container body and baffle according to a preferred embodiment of the present invention.
Figure 2B:
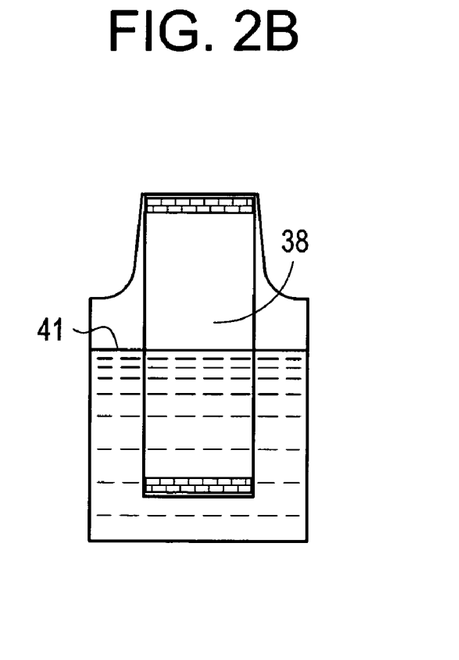
FIG. 2B is a side cutaway schematic view of a container body and baffle according to a preferred embodiment of the present invention.

FIGS. 2A and 2B show a schematic combination container body 20 and baffle 30. The container body 20 includes sidewalls 21, top surface 22, bottom surface 23 and opening 24. As shown in the figures, the container body is generally cylindrical. The tubular baffle 20 is shown in its inserted state in FIGS. 2a and 2b. The baffle includes sidewalls 31, a top or first end region 32, top or first opening 33, top or first pierceable seal 34, bottom or second end region 35, second or bottom opening 36 and bottom or second pierceable seal 37. As shown in FIG. 2A, the top and bottom or pierceable seals 34 and 37 are intact and prevent the liquid 40 from entering the baffle until the reagent liquid is ready for use.

FIG. 2B is identical to FIG. 2A except the seals are shown schematically as pierced. As explained above, the seals may be pierced with the metering tip. Upon piercing, liquid will enter into the baffle interior 38 and fill the baffle until it is level with the liquid level in the container. The liquid reagent is then ready for use.

Figure 3A:
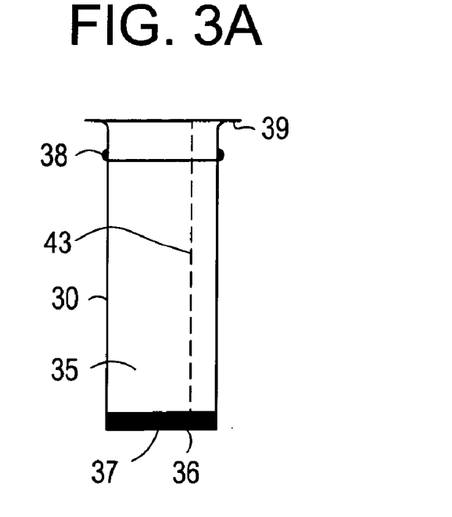
Figure 3B:
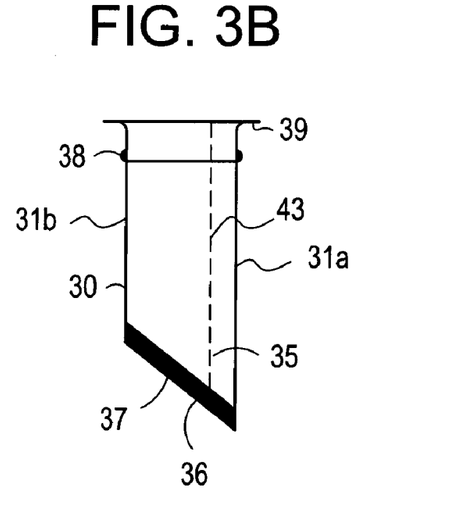
Figure 4:
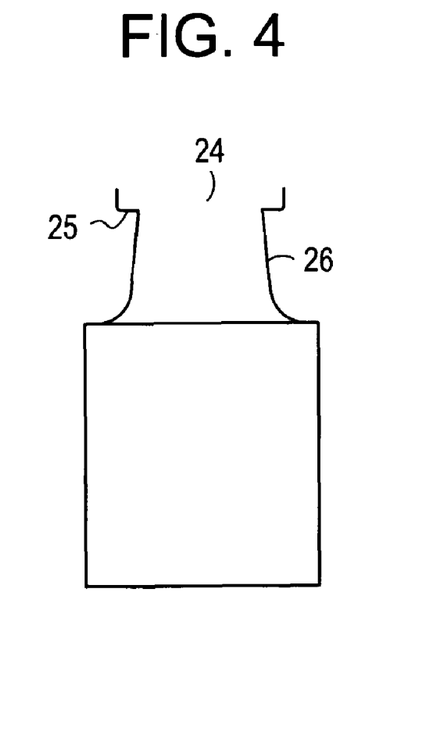
FIG. 4 is a side cutaway schematic view of a container body according to a preferred embodiment of the present invention.
Figure 5:
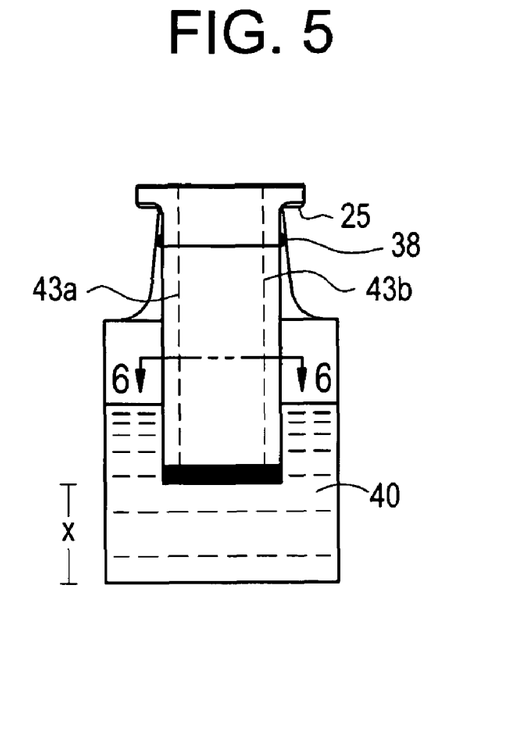
FIG. 5 is a side cutaway schematic view of a container body and baffle according to a preferred embodiment of the present invention.

A preferred manufacturing process is shown in FIGS. 3-5. As shown in FIGS. 3A and B, a baffle tube 30 has the second opening 36 sealed with a pierceable seal material 37, such as Surlyn®. In the preferred embodiment shown in FIG. 3B, the bottom opening of the baffle tube is formed at an angle. That is, sidewall 31a is longer than sidewall 31b. In this embodiment, the longer sidewall can touch the bottom of the container and liquid will still be able to enter after the seal is broken. The baffle tube also includes an indentation, such as a crease or seam 43 to provide an air gap between the baffle sidewall and container opening. A single crease or seam 43 is shown in phantom in FIGS. 3A and 3B. In another embodiment, shown in FIGS. 5 and 6, a double crease or seam is provided to provide two air gaps. This is most clearly seen in FIG. 6 which is a cross section taken along lines 6-6 in FIG. 5. As FIG. 6 clearly shows two air gaps 43a and 43b are provided, one on each side of the baffle.

The baffle tube is inserted into the liquid reagent bottle after it is filled. The Surlyn® seal prevents the liquid reagent 40 from entering the tube until the reagent supply is loaded on an analyzer. By using varying length baffle tubes, the distance "x" from the bottom of the container to the top of the liquid can be selected and foam in the baffle can be controlled without changing the bottle dimensions or using more reagent in the bottle. As explained above, the preferred dimension "x" is $\leq 2$ mm, more preferably around 1 mm. The baffle tube shown in FIG. 4 includes nibs or protrusions 38 that work in connection with the opening 24 of container 20 as explained in connection with FIG. 5. The baffle tube also includes a lip 39 that extends outwardly from the center of baffle 30.

An empty container 20 is shown in FIG. 4. In the embodiment shown in FIG. 4, the opening 24 is on a neck 26 which includes a lip 25 that is used in connection with the securing of the baffle tube to the container. As shown in FIG. 4, the lip 25 extends outwardly from the center of the opening.

As shown in FIG. 5, the baffle tube is placed into the bottle during manufacture with the seal already in place. The tube design interfaces to the container so that the lip 39 at the top of the tube interfaces or mates with the lip 25 on the opening of the container. The anti-backup protrusion (nib) 38 on the baffle tube 30 will prevent the tube from lifting during the assembly process. The Surlyn® used to seal the container will also be bonded to the top of the tube in the same operation preventing any liquid from entering the tube during shipment.

Figure 6:
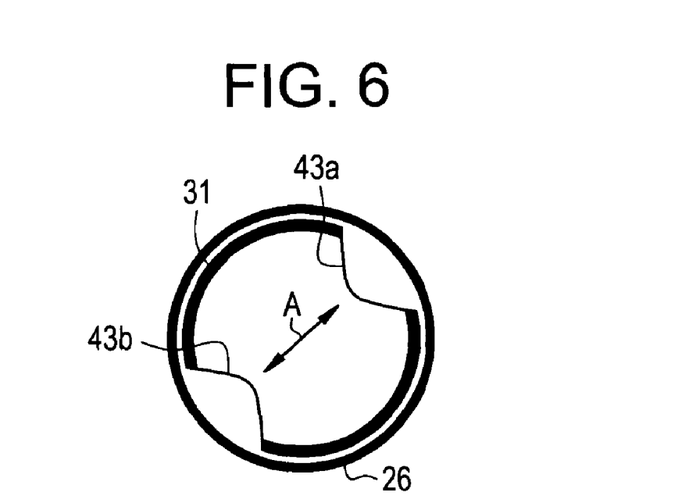
FIG. 6 is a top cross-sectional schematic view of the opening of the container and baffle taken along lines 6-6 of FIG. 5 according to a preferred embodiment of the present invention.

FIGS. 3 and 5 also show the gap formed by seam or crease 43 (FIG. 3) or seams or creases 43a, b (FIG. 5) in the sidewall of the baffle that is pierced to provide equalization in air pressure between the interior of the baffle (which will be at ambient when the seal covering the first opening is pierced) and the interior of the container. In the embodiment shown in FIG. 3, the sealed vent is a single vent. As described above, in the embodiment shown in FIGS. 5 and 6, there are two sealed vents formed by crease or seams 43a and 43b. In FIG. 6, the vents formed by crease or seam 43a and 43b are located directly across from each other in the direction "A" the container will travel in a diagnostic analyzer. This arrangement will assist in those embodiments where a aspirating/dispensing tip is used to pierce the seal.

In operation, the sealed baffle tube is generally below the surface of the liquid when a reagent supply is loaded on an analyzer. This prevents any foam from entering the tube during shipment and storage of the reagent pack or supply. Once the reagent pack or supply is loaded on the analyzer, the seals covering the first and second openings are pierced in a manner described above to allow liquid to enter the tube. Also, the seal on the baffle tube sidewall is pierced. In those embodiments where a tip is used to remove or pierce the seal, the reagent pack is rotated in direction A as shown in FIG. 6. This allows the tip to line up with the protruding seal. The tip can then be lowered to pierce the seal.

At this point, foam could form in the tube if the reagent source or pack is unloaded and reloaded on the analyzer but this is expected to be an infrequent event. If a user removes the pack and handles it in a manner that would create foam in a reagent pack, the baffle tube will also act as a baffle to reduce foam formation.

If there is extensive foam in the bottle, the reagent in the reagent pack may be used quickly enough for the liquid level to fall below the bottom opening of the baffle tube before the foam fully dissipates. Literature shows that foam and bubbles form stable structures so the tube should prevent foam from reforming in the center of the liquid. This should assure that the liquid remains clear of foam. If fluid does not go below the bottom opening of the baffle tube after all tests are processed, foam can not be introduced into the inner chamber. By having a higher residual dead volume in the outer chamber, the fluid remaining in the bottle after all tests are processed could (by design) be higher than this lower shelf.

Figure 7:
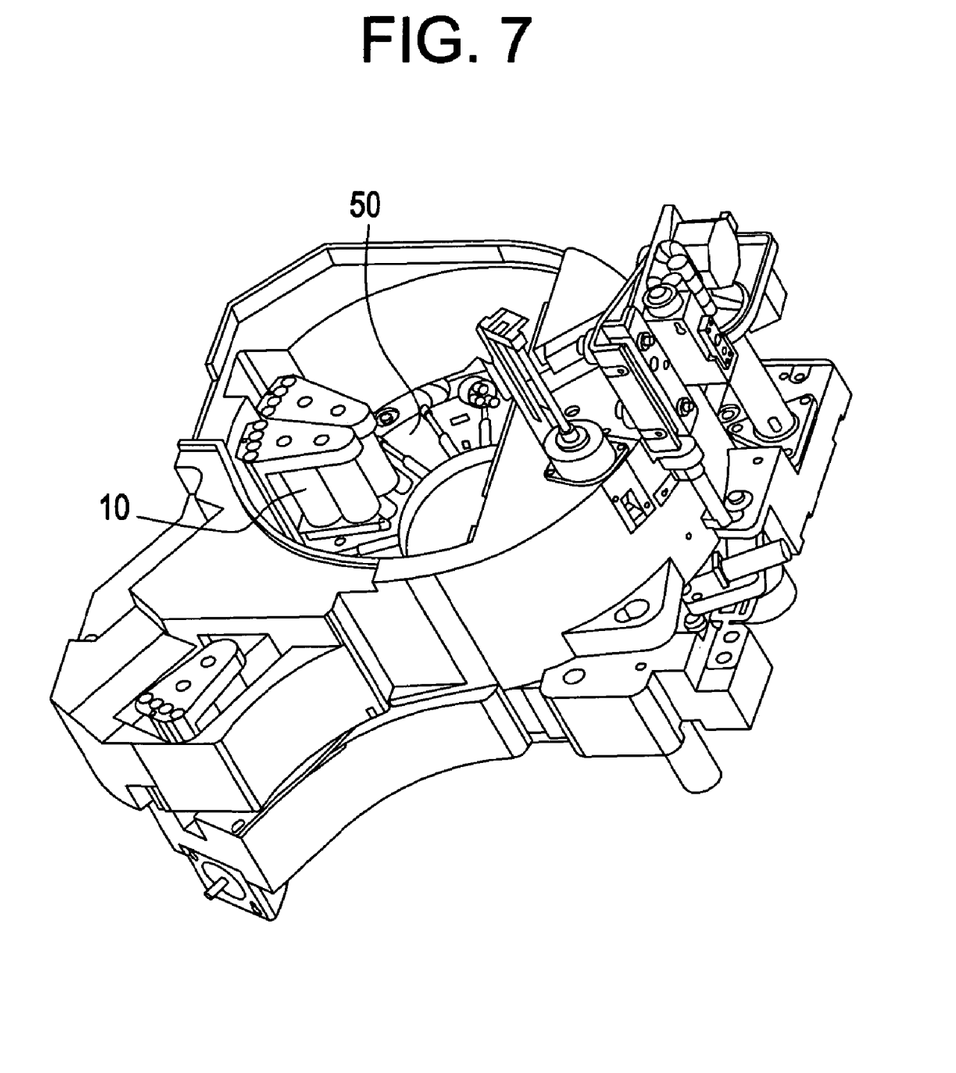
FIG. 7 is a perspective view of a reagent storage unit of a clinical analyzer according to a preferred embodiment of the present invention, showing a carousel for rotating the reagent packs.

FIG. 7 shows the reagent packs in a reagent storage unit of a clinical analyzer. The reagent packs 10 (slidable shutter closures not shown) are located on a conveyor 50, which rotates the reagent packs past various stations.

Figure 8:
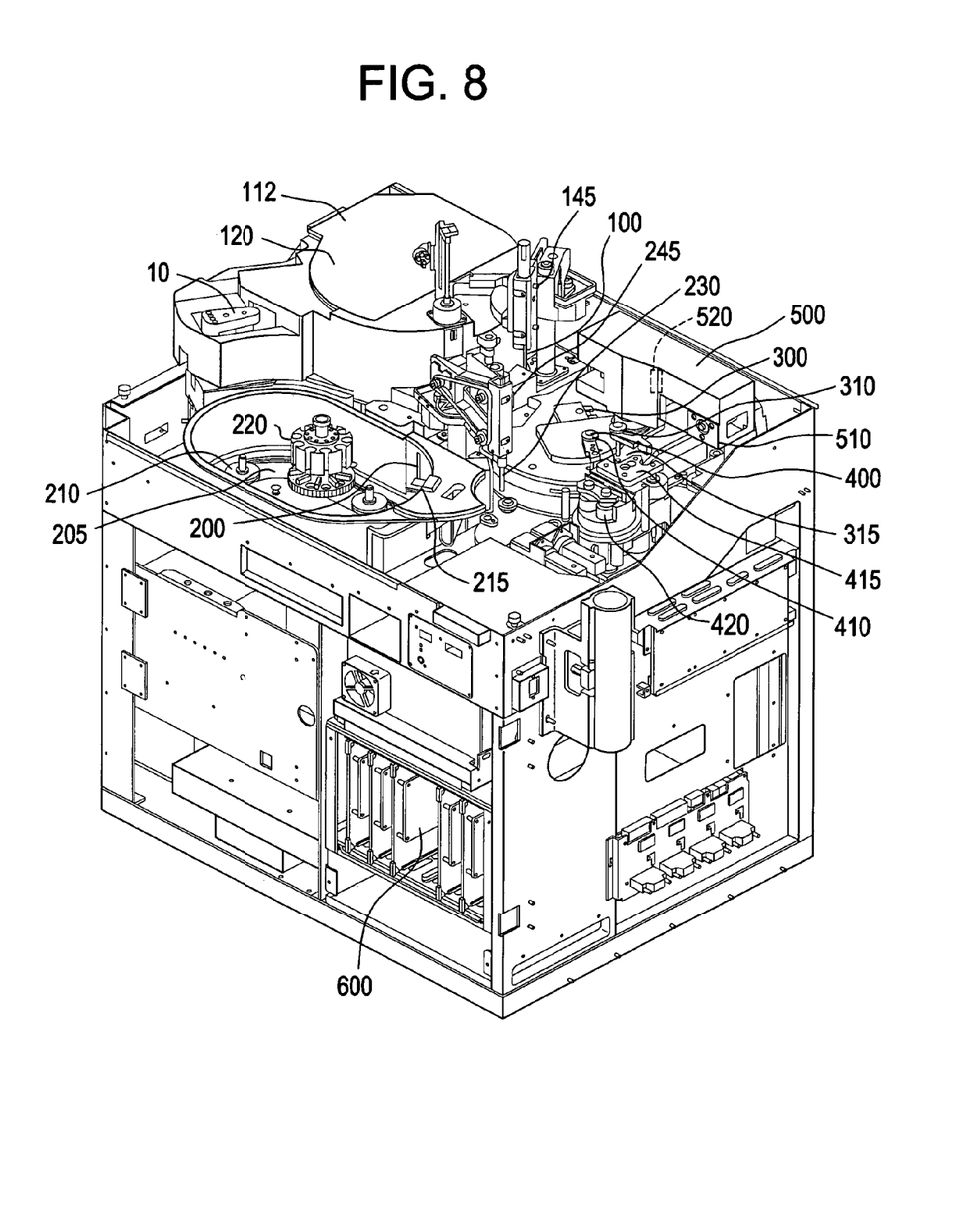
FIG. 8 is a perspective view of a diagnostic analyzer usable with the present invention.

FIG. 8 shows a preferred clinical analyzer that can use the opener/closer of reagent packs according to one embodiment of the present invention. The type of analyzer is described in more detail in U.S. Ser. No. 09/482,599 filed Jan. 13, 2000, the contents of which are incorporated by reference. As shown in FIG. 8, reagent packs 10 are initially external to the system but they are components that are manipulated by the reagent source. Reagent packs 10 are configured to contain the reagents necessary to conduct an assay. Typically, they include one or more antigenic or antisera components used to combine with the analyte and provide adhesion to or with a reaction vessel.

The reagent source includes autoload station 110 which shuttles reagent packs to the reagent supply substation 112 by any suitable drive mechanism such as a chain and sprocket, belt and pulley, gear train, linked belt mechanism, a driven series of mechanical links such as pawl links, or the like. The reagent source further includes a reagent supply cooler 120 that cools the interior of the reagent supply substation according to the functional requirements of the reagents (typically, 3-15° C., preferably 4-10° C.). In this way, reagent supply cooler 120 maintains reagents and reaction vessels at the appropriate humidity and temperature.

The reagent source further includes a reagent metering arm 145 having a reagent probe 100 movably attached to it. Reagent metering arm 145 is pivotable so that it can position the reagent metering probe 100 in position to dispense reagent or diluent into a reaction vessel. Reagent metering probe 100 aspirates, transports, and dispenses reagent and/or diluent into reaction vessel. It is generally configured so that it also moves in a vertical direction to dip into the opened reagent packs 10 and lower itself into the vicinity of the reaction vessel (well). This is accomplished by any of the well known mechanisms for affecting vertical motion such as gear train with step motor, belt and pulley assembly, pneumatic or hydraulic lifts, or the like. A stepper motor with fine steps (at least about 390 steps per cm of vertical motion are desired) connected to a rack and pinion drive is the preferred mechanism for regulating vertical motion. Where pivoting is required, a stepper motor with fine steps is also preferred (generally, at least about 1720 steps per revolution of the shaft used to rotate the probe or probe arm are desired) with the pinion comprising or attached to the outer diameter of the shaft that is rotated. Control of stepper motors, and hence probe and mechanism movement, is accomplished by techniques well known in the art such as those described in U.S. Pat. No. 5,646,049 which is incorporated herein by reference.

In operation, the reagent metering probe 100 aspirates and dispenses liquids via connection to a fluidics systems comprised of valves, pumps, tubing, and the like. It is preferably charged by vacuum and can disperse by release of vacuum or by pressurization.

Sample supply source loads and meters sample to the appropriate reaction vessels (preferably, wells not shown). It is also capable of providing input to the data processing systems via bar code reader 200 that reads bar codes that may be placed on patient sample vessels such as test tubes and the like. The sample supply source also includes a number of subsystems and components. The sample supply subsystem is one which is comprised of a bar code reader 200 for inputting sample identification data as described above and a sample tray conveyor 205, one or more sample tray transports 210, and positioner 215 for moving sample to the sample metering station adjacent to the sample positioner (i.e. the position into which proboscis 230 is lowered, as described below).

The sample tray conveyor 205 can be any conveyor system for moving vessels and can employ an electrically or mechanically movable magnetic drive that propels a carousel 220 atop a sample tray transport 210 having a magnetic or ferrous component attractive to the magnetic drive. Alternatively, the sample tray conveyor 205 can comprise a motor driven chain and sprocket mechanism, a driven series of mechanical links such as pawl links, a belt driven system or the like. The preferred sample tray conveyor is an elliptical magnetically driven tracked system. In this system, the sample tray is preferably a carousel 220 that sits atop a transport 210 that has a piece susceptible to magnetic attraction. This enables it to be moved around the ellipse through the rotation of a magnetic field around the perimeter of the elliptical track from a position beneath the sample trays. In this configuration, the outer diameter of the sample tray can be geared so that the tray can be rotated about its own central axis by a geared piece such as positioner 215 adjacent to the bar code reader 200 (or at any other convenient location around the exterior of the elliptical track).

The sample metering subsystem aspirates samples and dispenses them into reaction vessels via proboscis 230. The proboscis and its related metering arm 245 are preferably similar in design to the reagent metering arm 145 described above. Disposable tips (not shown) through which sample can be aspirated and dispensed are preferably fitted on the proboscis and are disposed after each aspiration and delivery of sample. The tips are preferably conical with the apex of the cone pointed toward down. Appropriate robotic commands are used to position the proboscis over the tips and then temporarily attach the tips via force (injection of the proboscis into the hollow portion of the tip). For convenience, a supply of tips can be maintained on a tip supply carousel (not shown). The tips can likewise be removed by raising the proboscis drive to its top most travel, activating an ejector sleeve (not shown). Generally, disposable tips are comprised of a molded thermoplastic such as polyethylene or polypropylene. Such tips avoid direct and repeated contact of sample and a singular proboscis end.

In operation, the sample metering subsystem functions similarly to that of the reagent metering system. Sample, loaded on sample carousel 220 is driven to a location reachable by the proboscis 230. After having loaded a disposable tip onto the proboscis, the system pivots the proboscis directly overhead a sample vessel. The proboscis is then lowered into a vessel such as a tube on the carousel where it aspirates a quantity of sample sufficient for the assay to be conducted. The proboscis is then pivoted to a position that is overhead a well residing in outer ring (not shown) where the sample is dispensed. It is preferable that the sample is dispensed into the well before reagent has been dispensed into the well. The proboscis can then be used to validate the proper metering of the sample into the well. This is accomplished by fitting the proboscis with a sensor such as an optical sensor on sample metering arm 245. The sensor (not shown) is in communication with a transducer (not shown) and the data processing system 600. The sensor preferably detects the level of the sample by pressure differential, through capacitance, or reflected energy as is known in the art. An optical sensor can also be used to home the proboscis to its proper position. After metering and measuring the sample, reagent is preferably dispensed into the well as described above. Mixing of sample and reagent is accomplished by dispensing reagent into the well containing sample with sufficient velocity to give partial mixing.

Some assays require dilution of the sample. When this is the case, sample is first metered into a dilution vessel that is preferably substantially similar to the wells previously described. Proboscis 230 is used to meter the sample as in other assays.

In the processing system, reaction wells containing sample, reagent, and (optionally) diluent are mixed with signal reagent and incubated in incubator 300. Chemiluminescence or other appropriate signal generation of the reaction of sample analyte and reagent(s) is also read in this system. Well wash arm 310 and well wash probe 315 are the principle components of the well wash subsystem whose function is to wash the wells and remove sample and unbound reagent (analyte is bound to the reaction vessel along with reagents that manifest the signal that is read later). The temperature and humidity are controlled within incubator 300 for a time and at a temperature appropriate to the assays being performed. Incubation time can differ from assay to assay and is under the control of the data processing system.

Returning to the well wash subsystem, after appropriate incubation, well wash probe 315 (which is preferably similar in design to the reagent probe 100) is manipulated so that it aspirates and dispenses sample and unbound reagent out of the reaction wells and then dispenses wash liquid into the wells, aspirates and dispenses again. Thus, to this point within the reaction wells, reagent and analyte have reacted and have been adhered to the well. The well wash arm has removed materials that have not reacted and/or could otherwise interfere with sample reading.

It is also possible to configure such an instrument so that the unmeasured materials would adhere to a reaction vessel and the contents of the vessel would be further processed or be subject to some reading. In such a case they would then have to be aspirated and dispensed to another vessel.

Upon completion of well washing, the well wash arm 310 articulates movably attached well wash probe 315 to a position to aspirate sample and unbound reagent and dispense wash liquid to the reaction vessel. Generally, wash liquid is dispensed as the well wash probe 315 is lifted out of the reaction vessel. The signal reagent subsystem comprises signal reagent arm 410, signal reagent probe 400, signal reagent (packs) 420, and prime/pump assembly 415 as its major components. Signal reagent probe 400 (which is preferably similar in design to the other probes already described), movably attached to signal reagent arm 410 aspirates, transport, and dispenses signal reagent from signal reagent pack 420 to the wells. Signal reagent arm 410 is fitted to a prime, pump assembly 415 for this purpose. Signal reagent is a composition that contains a component that produces a signal upon combination with the reacted reagent/sample combination (e.g., luminol derivatives). Luminometer 500 is comprised of a fiber optic bundle 510 that communicates with photomultiplier 520, which is in further communication with data processing system 600. In operation, the fiber optic bundle 510 is positioned over the sample with mixed reagent and, optionally, diluent. Chemiluminescent signals generated by the reacting reagent/sample combination are then transmitted to the photomultiplier that converts the light signal to an electrical signal for processing according to conventional digital techniques. An internal reference (not shown) can be used for calibration of the luminometer 500.

Data processing system 600 is an integrated array of circuitry used to coordinate the function of the systems and subsystems, conduct system diagnostics, calibrate instrumentation, record results, and analyze results. It includes well known processing devices such as microprocessors and may be in electronic communication with any number of external processing systems. For example, it may be linked through a local area network to other analytical instrumentation so that tests are scheduled and results are compiled and reported for a number of different assays, some of which are not conducted on the instrument described here.

The method of reducing or eliminating foam according to the present invention can be implemented by a computer program, having computer readable program code, interfacing with the computer controller of the analyzer as is known in the art.

It will be apparent to those skilled in the art that various modifications and variations can be made to the compounds, compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

We claim:

1. A method for reducing or eliminating the aspiration of foam into a metering probe comprising:
   providing a reagent supply container having a liquid reagent therein, wherein the reagent supply container comprises:
   (i) a container having
      a container body having a top portion, a bottom portion and an opening for adding the liquid to or removing the liquid from the container body; and
      a hollow baffle located within the container with first and second openings therein, the first opening being sealed and covered with a first pierceable seal and the second opening being sealed and covered with a second pierceable seal, wherein the first opening of the baffle is at least partially aligned with the opening of the container, and
   (ii) a closure which is movable away from the opening of the container to be in an open position and movable into contact with the opening to be in a closed position, wherein the second opening of the baffle is submerged in the liquid;
   providing a metering probe movable in a direction toward and away from the reagent supply container;
   moving the closure away from the opening of the container;
   piercing both seals covering the first and second openings of the baffle allowing liquid to enter the baffle from the end of the baffle submerged in the liquid thereby providing a foam reduced or foam free zone;
   moving the metering probe into the first opening of the baffle and into contact with the liquid in the baffle;
   aspirating a selected amount of liquid in the baffle; and
   moving the metering probe out of the baffle.

2. A method for according to claim 1, wherein the step of piercing both seals is performed by the tip of the metering probe.

3. A method as claimed in claim 1, wherein the baffle has sidewalls with the first opening at a first end region and the second opening at a second end region, wherein the first end region of the baffle contacts the opening of the container body during transport.

4. A method as claimed in claim 3, wherein the baffle forms a liquid tight seal with the opening of the container body during transport.

5. A method as claimed in claim 3, wherein the baffle contacts the opening of the container at the sidewalls in the vicinity of the first opening.

6. A method as claimed in claim 5, wherein the second end region of the baffle extends into the container at a location away from the opening of the container.

7. A method as claimed in claim 6, wherein the second opening of the baffle is located in the vicinity of the bottom of the container.

8. A method as claimed in claim 7, wherein the second opening is two millimeters or less from the bottom of the container.

9. A method as claimed in claim 7, wherein the second opening is around one millimeter or less from the bottom of the container.

10. A method as claimed in claim 1, wherein the first baffle opening is located in the vicinity of the container opening and wherein the pierceable seal covering the first baffle opening also covers the container opening.

11. A method as claimed in claim 3, further comprising an opening to allow air into the portion of the container outside of the baffle.

12. A method as claimed in claim 11, wherein the opening is a gap between the first end region of the baffle and the opening of the container.

13. A method as claimed in claim 12, wherein the opening is formed by an indentation in the sidewalls of the baffle.

14. A method as claimed in claim 13, wherein the indentation is a crease that runs along at least a portion of the length of the baffle sidewall.

15. A method as claimed in claim 11, wherein the opening is in the sidewall of the baffle located in the first end region, and wherein the first end region of the baffle forms a liquid tight seal with the opening of the container body.

16. A method as claimed in claim 15, wherein the opening is covered with a pierceable seal.

* * * * *